(12) United States Patent
Reuter et al.

(10) Patent No.: US 7,442,407 B2
(45) Date of Patent: Oct. 28, 2008

(54) TANTALUM AND NIOBIUM COMPOUNDS AND THEIR USE FOR CHEMICAL VAPOUR DEPOSITION (CVD)

(75) Inventors: Knud Reuter, Krefeld (DE); Jörg Sundermeyer, Marburg (DE); Alexei Merkoulov, Freiburg (DE); Wolfgang Stolz, Marburg (DE); Kerstin Volz, Dautphetal (DE); Michael Pokoj, Fernwald (DE); Thomas Ochs, Kirchheim-Betziesdorf (DE)

(73) Assignee: H.C. Starck GmbH (DE)

( * ) Notice: Subject to any disclaimer, the term of this patent is extended or adjusted under 35 U.S.C. 154(b) by 294 days.

(21) Appl. No.: 11/482,397

(22) Filed: Jul. 7, 2006

(65) Prior Publication Data

US 2007/0042213 A1 Feb. 22, 2007

(30) Foreign Application Priority Data

Jul. 15, 2005 (DE) .................... 10 2005 033 102

(51) Int. Cl.
*B05D 5/12* (2006.01)
*C07F 517/00* (2006.01)

(52) U.S. Cl. .................. 427/124; 427/123; 548/101
(58) Field of Classification Search ............... 427/123, 427/124; 548/101
See application file for complete search history.

(56) References Cited

U.S. PATENT DOCUMENTS

| 6,593,484 B2 | 7/2003 | Yasuhara et al. |
| 2004/0142555 A1 | 7/2004 | Kamepalli et al. |

FOREIGN PATENT DOCUMENTS

WO    WO-00/65123    11/2000

OTHER PUBLICATIONS

Kaloyeros et al., "Tantalum Nitride Films Grown by Inorganic Low Temperature Thermal Chemical Vapor Deposition," Journal of The Electrochemical Society, 146(1), 1999 (pp. 170-176).
Tsai et al., "Metalorganic chemical vapor deposition of tantalum nitride by tertbutylimidotris(diethylamido)tantalum for advanced metallization," Appl. Phys. Lett. vol. 67, No. 8, Aug. 21, 1995 (pp. 1128-1130).
Chiu et al., "Deposition of tantalum nitride thin films from ethylimidotantalum complex," Journal of Materials Science Letters, 11, 1992 (pp. 96-98).
Fix et al., "Chemical Vapor Deposition of Vanadium, Niobium, and Tantalum Nitride Thin Films," Chem. Mater., vol. 5, No. 5, 1993 (pp. 614-619).
Bleau et al., "Molecular precursors for the CVD of niobium and tantalum nitride," Polyhedron, vol. 24, 2005 (pp. 463-468).
Hieber, "Structural and Electrical Properties of Ta and Ta Nitrides Deposited by Chemical Vapour Deposition," Thin Solid Films, vol. 24, 1974 (pp. 157-164).

*Primary Examiner*—Jafar Parsa
(74) *Attorney, Agent, or Firm*—Connolly Bove Lodge & Hutz LLP

(57) ABSTRACT

Tantalum and niobium compounds having the general formula (I) and their use for the chemical vapour deposition process are described:

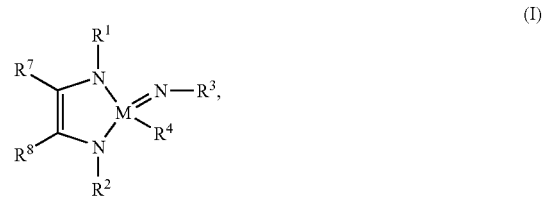

wherein
M stands for Nb or Ta,
$R^1$ and $R^2$ $C_1$ to $C_{12}$ alkyl, $C_5$ to $C_{12}$ cycloalkyl, $C_6$ to $C_{10}$ aryl radicals, 1-alkenyl, 2-alkenyl, 3-alkenyl, triorganosilyl radicals —$SiR_3$, or amino radicals $NR_2$
$R^3$ is $C_1$ to $C_8$ alkyl, $C_5$ to $C_{10}$ cycloalkyl, $C_6$ to $C_{14}$ aryl radical, or $SiR_3$ or $NR_2$,
$R^4$ denotes Cl, Br, I, NIH—$R^5$ where $R^5$ is $C_1$ to $C_8$ alkyl, $C_5$ to $C_{10}$ cycloalkyl or $C_6$ to $C_{10}$ aryl radical, or O—$R^6$ where $R^6$=optionally substituted $C_1$ to $C_{11}$ alkyl, $C_5$ to $C_{10}$ cycloalkyl, $C_6$ to $C_{10}$ aryl radical, or —$SiR_3$, or $BH_4$, or an allyl radical, or an indenyl radical, or an benzyl radical, or an cyclopentadienyl radical, or —NIR—NR'R" (hydrazido (-1), wherein R, R' and R" have the aforementioned meaning of R, or $CH_2SiMe_3$, pseudohalide, or silylamide —$N(SiMe_3)_2$, and
$R^7$ and $R^8$ are H, $C_1$ to $C_{12}$ alkyl, $C_5$ to $C_{12}$ cycloalkyl or $C_6$ to $C_{10}$ aryl radicals.

13 Claims, No Drawings

TANTALUM AND NIOBIUM COMPOUNDS AND THEIR USE FOR CHEMICAL VAPOUR DEPOSITION (CVD)

CROSS-REFERENCE TO RELATED APPLICATION

This application claims priority under 35 U.S.C. §119(a-e) to German application DE 10 2005 033102, filed Jul. 15, 2005.

FIELD OF THE INVENTION

The present invention concerns special novel tantalum and niobium compounds, their use for the deposition of tantalum- or niobium-containing coatings by chemical vapour deposition and the tantalum- or niobium-containing coatings produced by this process.

BACKGROUND OF THE INVENTION

Ta— and Ta—N-based mixed system coatings for use in Si microelectronics are currently produced by means of plasma-based deposition methods (physical vapour deposition (PVD)). In view of the extreme requirements for ever more highly integrated switching circuits, e.g. uniform coating deposition on textured surfaces, PVD processes are increasingly being pushed to the limits of what is technically feasible. For these applications, chemical gas phase deposition methods (chemical vapour deposition (CVD)) through to film deposition with atomic layer precision using a special CVD method known as atomic layer deposition (ALD) are increasingly coming into use. For these CVD processes the appropriate chemical starting materials for the individual elements must naturally be available for the coatings that are required in each case.

At present, halides such as e.g. $TaCl_5$, $TaBr_5$, see WO 2000065123 A1, A. E. Kaloyeros et al., *J. Electrochem. Soc.* 146 (1999), p. 170-176, or K. Hieber, *Thin Solid Films* 24 (1974), p. 157-164, are mainly used for the CVD of Ta-based coating structures. There are a number of disadvantages associated with this practice. Firstly, halogen radicals are undesirable in many ways for the formation of complex coating structures because of their caustic/corrosive properties, and secondly tantalum halides exhibit disadvantages due to their low volatility and difficult processing characteristics as high-melting solids. Simple tantalum(V) amides, such as e.g. $((CH_3)_2N)_5Ta$, are likewise proposed, see e.g. Fix et al., *Chem. Mater.*, 5 (1993), p. 614-619. However, with the simple amides only certain decomposition ratios of Ta to N can usually be established, which make the accurate control of the individual concentrations of elements in the coatings more difficult. In many cases Ta(V) nitride films are formed (see e.g. Fix et al.: $Ta_3N_5$) rather than the desired electrically conductive Ta(III) nitride coatings (TaN). Furthermore, the films produced with these starting materials very often exhibit high, undesirable concentrations of carbon. For that reason Tsai et al., *Appl. Phys. Lett.* 67(8), (1995), p. 1128-1130, proposed t-BuN=Ta(NEt$_2$)$_3$ in TaN CVD at 600° C. Because of its relatively low volatility, this compound requires a high plant temperature and is therefore not very compatible with the typical production processes for integrated switching circuits. Other, similar tantalum amide imides have also been proposed, see e.g. Chiu et al., *J. Mat. Sci. Lett.* 11 (1992), p. 96-98, with which, however, without additional reactive gas, high carbon contents were obtained in the tantalum nitride coatings. More recently, other tantalum nitride precursors have been proposed, e.g. by Bleau et al., *Polyhedron* 24(3), (2005), p. 463-468, which because of their complexity and laborious production exhibit disadvantages from the outset, or special cyclopentadienyl compounds, which either inevitably lead to TaSiN (not tantalum nitride) or require an additional, not otherwise specified nitrogen source (Kamepalli et al., US Pat. Appl. Publ. 2004142555 A1, Priority Jan. 16, 2003, ATMI, Inc.). In U.S. Pat. No. 6,593,484 (Kojundo Chemicals Laboratory Co., Ltd., Japan) a suitable special tantalum amide imide is proposed, although the specified synthesis can only be reproduced poorly and with difficulty.

A considerable need can thus be identified for other, novel precursors for TaN coatings which do not have the aforementioned disadvantages or which at least bring about clear improvements.

SUMMARY OF THE INVENTION

The object underlying the present invention was therefore to provide such precursors.

The invention concerns complex tantalum amides having a DAD ligand which meets these requirements. DAD stands for radicals having the general structure (A) derived from 1,4-diazabutadiene

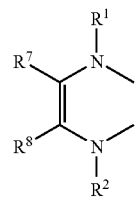

(A)

wherein
R$^1$ and R$^2$ mutually independently denote optionally substituted C$_1$ to C$_{12}$ alkyl, C$_5$ to C$_{12}$ cycloalkyl, C$_6$ to C$_{10}$ aryl radicals, 1-alkenyl, 2-alkenyl, 3-alkenyl, triorganosilyl radicals —SiR$_3$ or amino radicals NR$_2$, wherein R stands for a C$_1$ to C$_4$ alkyl radical, R$^7$ and R$^8$ mutually independently denote H, optionally substituted C$_1$ to C$_{12}$ alkyl, C$_5$ to C$_{12}$ cycloalkyl or C$_6$ to C$_{10}$ aryl radicals.

The invention also concerns the analogous niobium compounds which are suitable for example as CVD precursors for conductive niobium-nitride coatings (NbN).

The invention provides compounds having the general formula (I),

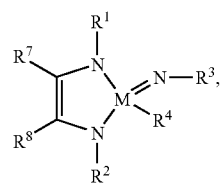

(I)

wherein
M stands for Nb or Ta,
R$^1$ and R$^2$ mutually independently denote optionally substituted C$_1$ to C$_{12}$ alkyl, C$_5$ to C$_{12}$ cycloalkyl, C$_6$ to C$_{10}$ aryl radicals, 1-alkenyl, 2-alkenyl, 3-alkenyl, triorganosilyl radicals —SiR$_3$ or amino radicals NR$_2$ wherein R stands for a C$_1$ to C$_4$ alkyl radical,
R$^3$ denotes an optionally substituted C$_1$ to C$_8$ alkyl, C$_5$ to C$_{10}$ cycloalkyl, C$_6$ to C$_{14}$ aryl radical, SiR$_3$ or NR$_2$, wherein R has the aforementioned meaning,
R$^4$ denotes halogen from the group comprising Cl, Br, I, or NH—R$^5$ where R$^5$=optionally substituted C$_1$ to C$_8$ alkyl, C$_5$ to C$_{10}$ cycloalkyl or C$_6$ to C$_{10}$ aryl radical, or O—R$^6$ where R$^6$=optionally substituted C$_1$ to C$_{11}$ alkyl, C$_5$ to C$_{10}$ cycloalkyl, C$_6$ to C$_{10}$ aryl radical, or —SiR$_3$, or BH$_4$, or an optionally substituted allyl radical, or an indenyl radical, or an optionally substituted benzyl radical, or an optionally substituted cyclopentadienyl radical, or —NR—NR'R" (hydrazido (−1), wherein R, R' and R" mutually independently have the cited meaning of R or CH$_2$SiMe$_3$, pseudohalide (e.g. —N$_3$), or silylamide —N(SiMe$_3$)$_2$, R$^7$ and R$^8$ mutually independently denote H, optionally substituted C$_1$ to C$_{12}$ alkyl, C$_5$ to C$_{12}$ cycloalkyl or C$_6$ to C$_{10}$ aryl radicals.

Unless otherwise specified, substituted in this context is understood to refer to a substitution with C$_1$ to C$_4$ alkoxy or di-(C$_1$ to C$_4$ alkyl) amino radicals.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

The tantalum and niobium compounds according to the invention can be used to produce tantalum- and/or niobium-containing metals, metal alloys, oxides, nitrides and carbides and mixtures thereof, and/or compounds in amorphous and/or crystalline form, by means of CVD, ALD (atomic layer deposition) and thermal decomposition. Such mixtures and compounds are used e.g. as dielectric coatings in capacitors and gates in transistors, microwave ceramics, piezo-ceramics, thermal and chemical barrier coatings, diffusion barrier coatings, hard material coatings, electrically conductive coatings, antireflective coatings, optical coatings and coatings for IR mirrors. One example of optical materials are Li tantalates and niobates. Examples of electrically conductive and corrosion-resistant coatings for electrodes are tantalum- and/or niobium-containing titanium and ruthenium mixed oxides. Tantalum and niobium compounds according to the invention are also suitable as precursors for flame pyrolysis for the production of powders.

Tantalum and niobium imides having the general formula (II) are preferred,

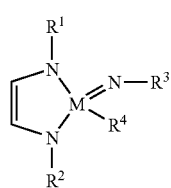

(II)

wherein

M stands for Ta or Nb,

R$^1$ and R$^2$ denote identical C$_1$ to C$_5$ alkyl or C$_5$ to C$_6$ cycloalkyl radicals, R$^3$ denotes a C$_1$ to C$_5$ alkyl, C$_5$ to C$_6$ cycloalkyl or optionally substituted phenyl radical, or SiR$_3$, or NR$_2$, wherein R stands for C$_1$ to C$_4$ alkyl, R$^4$ denotes a halogen from the group comprising Cl, Br, I, a radical NH—R$^5$ where R$^5$=C$_1$ to C$_5$ alkyl, C$_5$ to C$_6$ cycloalkyl or optionally substituted C$_6$ to C$_{10}$ aryl radical, or BH$_4$, or an optionally substituted allyl radical, or an indenyl radical, or an optionally substituted benzyl radical, or an optionally substituted cyclopentadienyl radical or an oxyalkyl radical.

Tantalum amide imides having tert-butyl-substituted DAD ligands displaying the structure (1) are particularly preferred:

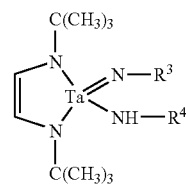

(III)

wherein

R$^3$ and R$^4$ mutually independently denote an identical or different radical from the group of C$_1$ to C$_5$ alkyl radicals, or C$_6$ to C$_{10}$ aryl radicals optionally substituted by one to three C$_1$ to C$_5$ alkyl groups, or SiR$_3$ or NR$_2$.

The compound having the structure (IV)

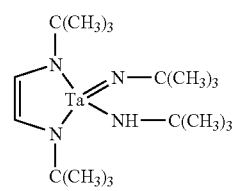

(IV)

is most particularly preferred.

The analogous compounds having formula (V)

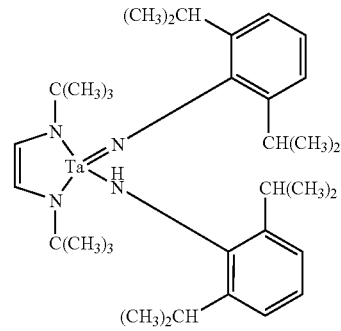

(V)

and the analogous compound having the structure (VI), which in particular is usually in dimeric form,

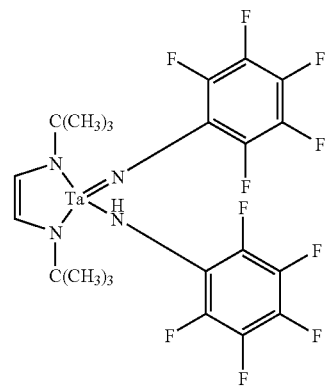

(VI)

are likewise most particularly preferred.

Other most particularly preferred compounds are those having the structure (III),

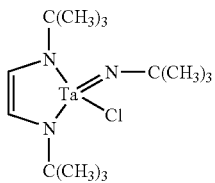
(VII)

the structure (VII),

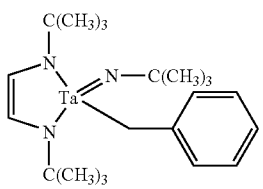
(VIII)

the structure (IX),

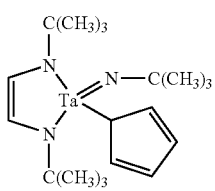
(IX)

and the structure (X).

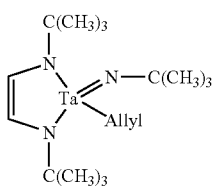
(X)

Particularly preferred compounds are moreover those having the general formula (XI),

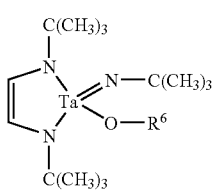
(XI)

wherein
$R^6$ denotes an optionally substituted $C_1$ to $C_{12}$ alkyl radical.

From this group the compound having the structure (XII) is particularly preferred.

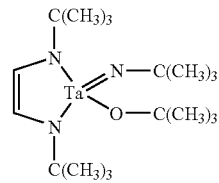
(XII)

Other preferred compounds are those having the general structure (XI),

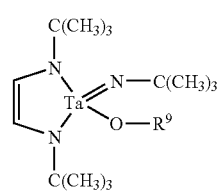
(XIII)

wherein
$R^9$ denotes a radical of an enolate having the formula (XIV),

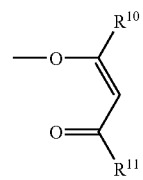
(XIV)

in which
$R^{10}$ denotes a $C_1$ to $C_4$ alkyl radical and $R^{11}$ is the same as $R^{10}$ or mutually independently denotes $OR^{10}$.

Alkyl or alkoxy stands independently in each case for a straight-chain, cyclic or branched alkyl or alkoxy radical, wherein the cited radicals can optionally be further substituted. The same applies for the alkyl portion of a trialkylsilyl or mono- or dialkyl amino radical or the alkyl portion of mono- or dialkyl hydrazines or mono-, di-, tri- or tetraalkyl silanes.

Within the context of the invention, $C_1$-$C_4$ alkyl stands, for example, for methyl, ethyl, n-propyl, isopropyl, n-butyl, sec-butyl, tert-butyl, $C_1$-$C_5$ alkyl stands in addition for example for n-pentyl, 1-methylbutyl, 2-methylbutyl, 3-methylbutyl, neopentyl(2,2-dimethylpropyl), 1-ethylpropyl, 1,1-dimethylpropyl, 1,2-dimethylpropyl, $C_1$-$C_6$ alkyl stands in addition for example for n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, $C_1$-$C_{12}$ alkyl stands in addition for example for n-heptyl and n-octyl, n-nonyl, n-decyl and n-dodecyl.

1-Alkenyl, 2-alkenyl, 3-alkenyl stand for example for the alkenyl groups corresponding to the above alkyl groups. $C_1$-$C_4$ alkoxy stands for example for the alkoxy groups corresponding to the above alkyl groups, such as e.g. methoxy, ethoxy, n-propoxy, isopropoxy, n-butoxy, sec-butoxy, tert-butoxy.

$C_5$-$C_{12}$ cycloalkyl stands for example for optionally substituted mono-, bi- or tricyclic aLkyl radicals. Examples are cyclopentyl, cyclohexyl, cycloheptyl, pinanyl, adamantyl, the isomeric menthyls, n-nonyl, n-decyl, n-dodecyl. Cyclopentyl and cyclohexyl are preferred. as $C_5$-$C_6$ cycloalkyl.

Aryl stands independently in each case for an aromatic radical having 6 to 14, preferably 6 to 10 skeletal carbon atoms, in which none, one, two or three skeletal carbon atoms per cyclic compound can be replaced by heteroatoms selected from the group comprising nitrogen, sulfur or oxygen, preferably however for a carbocyclic aromatic radical having 6 to 14, preferably 6 to 10 skeletal carbon atoms.

Examples of optionally substituted $C_6$-$C_{10}$ aryl are phenyl, 2,6-diisopropyl phenyl, o-, p-, m-tolyl or naphthyl.

The carbocyclic aromatic radical or heteroatomic radical can also be substituted with up to five identical or different substituents per cyclic compound, which are selected from the group comprising fluorine, cyano, $C_1$-$C_{12}$ alkyl, $C_1$-$C_{12}$ fluoroalkyl, $C_1$-$C_2$ fluoroalkoxy, $C_1$-$C_{12}$ alkoxy or di($C_1$-$C_8$ alkyl) amino.

The compounds according to the invention can be produced in a simple manner by reacting DAD ligand precursors having the general formula (B)

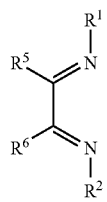

(B)

wherein $R^1$, $R^2$, $R^5$ and $R^6$ have the aforementioned meaning, in the presence of at least one reducing agent with Ta or Nb complexes having the general formula (C),

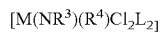

wherein

M stands for Ta or Nb

L stands for a ligand selected from aliphatic or aromatic amines, ethers, halide, preferably chloride, or nitriles, preferably acetonitrile, $R^3$ or $R^4$ have the aforementioned meaning, in a suitable solvent, preferably at a temperature of –20° C. to 120° C.

Possible examples of suitable reducing agents are non-noble metals such as e.g. Mg, Zn, Li, Na, Al, etc. Suitable solvents are for example ethers, such as e.g. THF, diethyl ether or 1,2-dimethoxyethane, dipolar-aprotic solvents, such as e.g. acetonitrile, N,N-dimethyl formamide or tert-amines or aliphatic or aromatic hydrocarbons, such as e.g. toluene, pentane, hexane, etc., and mixtures of these or mixtures with optionally other solvents. The Ta or Nb complexes having the general formula (C) [M(NR³)(R⁴)Cl₂L₂] can be produced by generally known processes in isolated form or in situ.

Moreover, it is also possible to reduce the DAD ligand precursor having the general formula (B) in advance in a suitable solvent with the reducing agent, such that solutions of the pre-reduced DAD ligands, such as, with Li as reducing agent for example, Li[DAD] or Li₂[DAD], are reacted with the solution of the complexes having the general formula (C). With a careful choice and control of the reaction temperature between –20° C. and 120° C. it is also possible to produce the compounds according to the invention in a one-pot synthesis, in which e.g. TaCl₅ is combined and reacted with the amine(s) $H_2NR^3$ or $H_2NR^4$, the reducing agent and the DAD ligand precursor having the general formula (B).

In order to isolate the compounds according to the invention, the solvent is removed by distillation, for example, under reduced pressure, and this can be followed by a further purification by washing and a subsequent drying. Such suitable processes are known to the person skilled in the art.

The invention also provides the use of compounds according to formula I as a precursor for tantalum nitride (TaN) coatings by means of chemical vapour deposition and the TaN coatings produced accordingly by CVD from the compounds having formula L. Compounds having formula II are preferably used in these processes, particularly preferably compounds having formula III, most particularly preferably compounds having formula IV to XII. The definition of the radicals here corresponds to the definitions given above.

The invention also provides substrates exhibiting a TaN or an NbN coating which is produced from compounds having formula I or preferably formula II with the aforementioned definitions for the various radicals.

The following points are to be regarded as technical advantages of the compounds proposed in the present invention:

1) The synthesis of the volatile Ta and Nb compounds does not require expensive lithium alkyls or amides.

2) The introduction of the DAD ligand as a CVD-compatible starting group for Ta(III) or Nb(III) coatings reduces the risk of an undesirable incorporation of C in the substrate coating.

3) Through the introduction of additional stable starting groups, such as e.g. cyclopentadienyl (Cp) or boronate (BH₄), the reduction of C incorporation in CVD is further encouraged.

4) In the combination with N starting materials, for example hydrazine derivatives (such as e.g. 1,1-dimethylhydrazine or tert-butylhydrazine), a selective modification of the coating composition is possible during CVD.

5) Selective influencing of the oxidation state of Ta(B) or Ta(V) compounds and their Nb analogues.

The invention also concerns the use of the Ta and Nb compounds according to the invention for the deposition of Ta- or Nb-containing coatings, optionally with incorporation of other compounds, for the defined establishment of certain concentrations of the various elements in the coating by means of chemical vapour deposition (CVD) with the following process steps: A suitable substrate, such as e.g. a Si wafer or a Si wafer already exhibiting other surface-textured single or multiple coatings, as are typically used for the manufacture of Si-based integrated switching circuits, is introduced into a CVD plant and heated to a temperature suitable for coating deposition in the range from 250° C. to 700° C. A carrier gas is loaded with the starting materials in defined concentrations, wherein inert gases such as e.g. N₂ and/or Ar, also in combination with inert, evaporated solvents such as e.g. hexane, heptane, octane, toluene or butyl acetate, can be used as the carrier gas, and reactive, e.g. reducing gases such as e.g. H₂ can also be added. The loaded carrier gas is passed for a defined exposure time over the surface of the heated substrate, the concentrations being adapted to the starting materials and the exposure time, with the proviso that a Ta- or Nb-containing coating is formed with a predefined coating thickness and a predefined composition on the surface of the substrate in amorphous, nanocrystalline, microcrystalline or polycrystalline form. Depending on the deposition rate, typical exposure times are, for example, a few seconds to several minutes or hours. Typical deposition rates can be from 0.1 nm/sec to 1 nm/sec, for example. Other deposition rates are also possible, however. Typical coating thicknesses are e.g. 0.1 to 100 nm, preferably 0.5 to 50 nm, particularly preferably 1 to 10 nm.

Within the context of CVD technology, in addition to the starting materials according to formula I, preferably formulae II to XIII, for the production of pure Ta or Nb metal coatings (Ta- or Nb-rich single coatings), Ta- or Nb-rich coatings and TaN— or NbN-containing mixed coatings, the following starting materials can also be used for selective establishment of the N concentration in TaN— or NbN-containing mixed system coatings—also referred to below as N starting materials: ammonia ($NH_3$) or $C_1$-$C_8$ monoalkylhydrazines, in particular tert-butylhydrazine ($^tBu$-NH—$NH_2$), and/or $C_1$-$C_5$-1,1-dialkylhydrazines, in particular 1,1-dimethyl-hydrazine (($CH_3$)$_2$N—$NH_2$), wherein the alkyl groups can be linear or branched. To influence the stability of the mixed system coatings that are produced in the subsequent high-temperature full cure steps in particular, the incorporation of other elements in the CVD deposition can be beneficial in order to influence the recrystallisation characteristics of the coating that is formed. The element Si is particularly suitable for use in Si-based integrated switching circuits. In addition to the aforementioned starting materials, the following starting materials for Si— also referred to below as Si starting materials—are advantageously used in CVD technology for the production of mixed system coatings containing Ta(or Nb)—N—Si: silane ($SiH_4$) and/or disilane ($Si_2H_6$) and/or $C_1$-$C_8$ monoalkyl silanes, in particular tert-butyl silane (tBu-$SiH_3$), and/or $C_1$-$C_8$ dialkyl silanes, in particular di-tert-butyl silane (t$Bu_2SiH_2$), and/or $C_1$-$C_8$ trialkyl silanes, in particular triethyl silane (($C_2H_5$)$_3$SiH), and/or $C_1$-$C_8$ tetraalkyl silanes, in particular tetraethyl silane (($C_2H_5$)$_4$Si), wherein the alkyl groups can be linear or branched.

The exact concentrations of the starting materials are determined in principle by the thermal decomposition characteristics of the individual starting materials in the CVD process. The starting materials are preferably used in the following molar ratios: N starting material/Ta or Nb starting material 0 to 20,000, Si starting materials/Ta or Nb starting material 0-100. The surface temperature of the substrate is preferably set in the range from 300° C. to 600° C. The overall pressure of carrier gas and starting materials is preferably established at pressures in the range from 10 hPa to 1000 hPa, the ratio of the partial pressure of the sum of all starting materials to the partial pressure of the carrier gas being between 0.0001 and 0.5. The deposition rate is preferably 0.05 nm/min to 50 nm/min.

The tantalum and niobium compounds according to the invention are also suitable as precursors for tantalum oxide ($Ta_2O_5$) coatings and niobium oxide (Nb2O5) coatings, which are of interest for microelectronics because of their high dielectric constants.

The examples below serve to illustrate the invention by way of example and should not be regarded as a limitation.

EXAMPLES

In the examples below the abbreviations and abbreviated compound names denote the following structures:
D$^t$BuAD=1,4-di-tert-butyl-1,4-diazabutadiene

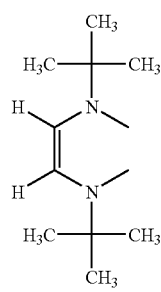

or its divalent radical
$^t$Bu=tert-butyl
$^t$BuN=tert-butyl imino=$^t$Bu-N=
Me=methyl
Py=pyridine
Bz=benzyl
AcAc=monovalent radical of the enolate form of acetyl acetone=

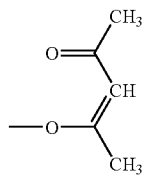

Cp=cyclopentadienyl
Ind=monovalent radical of indene

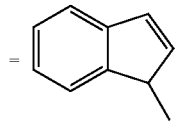

Dip=2,6-di-isopropyl phenyl

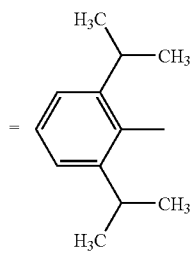

all=allyl

Example for the Production Not According to the Invention Intermediate Example A Production of $Li_2D^tBuAD$ 870 mg (125 mmol) of lithium were added to a solution of 10 g (60 mmol) of D$^t$BuAD in 200 ml of diethyl ether with cooling. After stirring for 8 h at 23° C., the orange-coloured solution was filtered. The solvent was then distilled off at 20 mbar and the residue dried in high vacuum for 48 h. Yield 10.8 g (almost quantitative).
Analysis:
$^1$H—NMR (δ against TMS, $C_6D_5CD_3$, 300 K, 200 MHz): 5.52 (s, 2H), 1.10 (s; 18H).

Intermediate Example B

Production of [Ta($^t$BuN)($^t$BuNH)$Cl_2$.2Py]

61.3 ml of $^t$BuNH$_2$ (587 mmol) in 50 ml of $CH_2Cl_2$ were added dropwise to a suspension of 21.0 g of $TaCl_5$ (58.7 mmol) in 200 ml of $CH_2Cl_2$ with cooling. The reaction mixture was then heated to 23° C. and stirred for 4 h. The suspension obtained was cooled again with an ice bath and a solution of 23.7 ml (294 mmol) of pyridine in 50 ml of $CH_2Cl_2$ was added. After stirring for 4 h at 23° C., 150 m of hexane were added to the reaction mixture and the solution obtained was filtered through celite. The residue was washed twice more with 100 ml of $CH_2Cl_2$/hexane 1:1 until it was colourless. The combined solutions were freed from all volatile components at 20 mbar, the residue was washed with hexane and dried. Pale yellow, microcrystalline product, yield 25.9 g (84% of theoretical), melting point >120° C. (decomposition).

Elemental Analysis

Calculated (%) for $C_{18}H_{29}N_4Cl_2Ta$ (M=553.31 g·mol$^{-1}$): C, 39.07; H, 5.29; N, 10.13. Found (%): C, 40.15; H, 5.17; N, 10.02.

MS-EI: 379 (M$^+$-2Py-Me, 20%), 323 (M$^+$-2Py-$(CH_3)_2$ $CCH_2$-Me, 42%), 41 (100%).

$^1$H-NMR (300.1 MHz, $CDCl_3$): δ=1.28 (s, 9H, NHC $(CH_3)_3$), 1.31 (s, 9H, NC$(CH_3)_3$), 7.44 (pseudo-t, 4H, m-$H_{py}$), 7.86 (tt, $J_1$=7.7 Hz, $J_2$=1.5 Hz, 2H, p-Hpy), 8.60 (broad s, 1H, NHC$(CH_3)_3$), 9.40 (dd, $J_1$=6.9 Hz, $J_2$=1.5 Hz, 4H, o-$H_{py}$)

$^{13}$C{$^1$H}-NMR ($CDCl_3$, 75 MHz, 300 K): 32.3 (NC $(CH_3)_3$), 33.9 (NHC$(CH_3)_3$), 56.4 (NHC$(CH_3)_3$), 64.8 (s, NC$(CH_3)_3$), 124.1 (m-Py), 139.2 (p-Py), 153.5 (o-Py).

Intermediate Example C

Production of [(D$^t$BuAD)($^t$BuN)Ta(μ-Cl)]$_2$ 43.8 ml of tert-butylamine (418.7 mmol) were added dropwise at 0° C. with stirring to a suspension of 50.00 g of $TaCl_5$ (139.6 mmol) in 300 ml of $CH_2Cl_2$. The reaction mixture was heated to 23° C. and stirred for 3 h at this temperature. 23.49 g (139.6 mmol) of DtBuAD were then added and the resulting suspension was stirred for 8 h. The mixture was then filtered following the addition of 150 ml of hexane. The volatile components were removed from the filtrate at 20 mbar and the residue then dissolved in 200 ml of THF. 1.94 g (279.2 mmol) of lithium powder were then added slowly with cooling (immediate dark brown coloration). After stirring for 8 h the solvent was evaporated off at 20 mbar and the residue extracted twice with 150 ml of diethyl ether each time. The solvent was evaporated off from the extract at 20 mbar. The residue was sublimated at 160° C./10$^{-4}$ mbar. Yield: 38.8 g (61% of theoretical), melting point 150.0° C.

Elemental analysis:

Calculated (%) for monomeric $C_{14}H_{29}N_3ClTa$ (M=455.81 g mol$^{-1}$): C, 36.89; H, 6.41; N, 9.22. Found: C, 36.39; H, 6.37; N, 9.18.

MS-EI: 455 (M$^+$, 9%), 440 (M$^+$-Me, 21%), 399 (M$^+$-$Me_2C$=$CH_2$, 7%), 384(M$^+$-Me-$Me_2C$=$CH_2$, 5%), 328 (M$^+$-Me-2•$Me_2C$=$CH_2$, 5%), 58 (100%)

$^1$H-NMR ($CD_6$, 300 MHz, 300 K): 6.07 (bs, 2H, CH-D$^t$BuAD), 1.47 (s, 9H, N$^t$Bu), 1.35 (s, 18H, $^t$Bu-D$^t$BuAD)

$^{13}$C{$^1$H}-NMR ($C_6D_6$, 75 MHz, 300 K): 103.8 (CH-D$^t$-BuAD), 65.7 (NCMe$_3$), 56.9 (CMe$_3$-D$^t$BuAD), 33.8 (NCMe$_3$), 31.1 (CMe$_3$-D$^t$BuAD)

IR (KBr, cm$^{-1}$): 3036(w), 1503(w), 1456(s), 1364(s), 1356 (w), 1285(s), 1217(s), 1146(m), 1113(w), 1069(w), 1038(w), 1026(w), 1018(w), 964(w), 870(m), 810(m), 770(s), 723(w), 567(w), 544(w), 511(w), 453(w).

Intermediate Example D

Production of [(D$^t$BuAD)($^t$BuN)Nb(μ-Cl)]$_2$ 500 mg of the pyridine complex from Example 19 were sublimated at 150° C./10$^{-4}$ mbar. Yield: 230 mg (56%). Melting point 188° C. Analysis analogous to intermediate Example E.

Intermediate Example E

Production of [(D$^t$BuAD)($^t$BuN)Nb(μ-Cl)]$_2$ 23.2 ml of tert-butylamine (222 mmol) were added dropwise at 0°C. with stirring to a suspension of 20.00 g of $NbCl_5$ (74 mmol) in 300 ml of $CH_2Cl_2$. The reaction mixture was heated to 23° C. and stirred for 3 h at this temperature. Then 12.5 g (74 mmol) of D$^t$BuAD were added and the resulting suspension was stirred for 8 h. The mixture was then filtered following the addition of 150 ml of hexane. The volatile components were removed from the filtrate at 20 mbar and the residue then dissolved in 200 ml of THF. 1.0 g (148 mmol) of lithium powder were then added slowly with cooling. After stirring for 8 h the solvent was evaporated off at 20 mbar and the residue extracted twice with 150 ml of diethyl ether each time. The solvent was evaporated off from the extract at 20 mbar. The residue was sublimated at 160° C./10$^{-4}$ mbar. Yield: 12.9 g (47% of theoretical), melting point 188.4° C.

Elemental analysis:

Calculated (%) for monomeric $C_{14}H_{29}N_3ClNb$ (M=367.77 g mol$^{-1}$): C, 45.72; H, 7.95; N, 11.43. Found (%): C, 45.88; H, 8.04; N, 11.41.

MS-EI: 367(M$^+$, 1%), 352(M$^+$-Me, 1%), 296(M$^+$-$Me_2C$=$CH_2$-Me, 1%), 58(100%).

$^1$H-NMR ($C_6D_6$, 300 MHz, 300 K): 6.08 (broad s, 2H, CH-D$^t$BuAD), 1.45 (s, 9H, N$^t$Bu), 1.38 (s, 18H, $^t$Bu-D$^t$-BuAD).

$^{13}$C{$^1$H}-NMR ($C_6D_6$, 75 MHz, 300 K): 106.0 (CH-D$^t$-BuAD), 57.7 (CMe$_3$-D$^t$BuAD), 32.4 (NCMe$_3$), 30.8 (CMe$_3$-DAD).

IR (KBr, cm$^-$): 3032(w), 1491(w), 1456(s), 1393(w), 1360 (m), 1263(s), 1246(w), 1215(s), 1155(w), 1144(w), 1092(w), 1061(w), 1036(w), 1026(w), 1017(w), 951(w), 870(m), 810 (m), 774(s), 723(w), 698(w), 669(w), 584(w), 569(m), 540 (w), 515(w).

EXAMPLES ACCORDING TO THE INVENTION

Example 1

Production of (D$^t$BuAD)($^t$BuN)TaCl as Pyridine Complex

A solution of 1.76 g (9.7 mmol) of $Li_2$D$^t$BuAD from intermediate example A in 20 ml of THF was added dropwise at −80° C. to a solution of 5.00 g (9.7 mmol) of $^t$BuN=TaCl$_3$.2Py (produced according to Lit. J. Sundermeyer, J. Putterlik, M. Foth, J. S. Field, N. Ramesar, *Chem. Ber.* 1994, 127, 1201-1212) in 20 ml of THF. After stirring for 30 min the dark-brown reaction mixture was heated and stirred for a further 10 h at 23° C. After distilling off all volatile components the residue was extracted twice with 10 ml of diethyl ether each time. The ether phases were combined, the ether distilled off and the yellow residue washed twice with 10 ml of hexane each time. Yield 2.11 g; in addition, a further 0.64 g were obtained by crystallising the mother liquor at −80° C. Total yield 2.75 g (53.1% of theoretical), melting point 142.8° C.

Elemental analysis:

Calculated (%) for $C_{19}H_{34}N_4ClTa$ (M=534.91 g·mol$^{-1}$): C, 42.66; H, 6.41; N, 10.47. Found (%): C, 42.27; H, 5.97; N, 10.19.

MS-EI: 455 (M$^+$Py, 15%), 440 (M$^+$Py-Me, 39%), 399 (M$^+$-Py-Me$_2$C=CH$_2$, 13%), 384 (M$^+$-Py-Me-Me$_2$C=CH$_2$, 2%), 343 (M$^+$-Py-2•Me$_2$C=CH$_2$, 1%) 328 (M$^+$-Py-Me-2•Me$_2$C=CH$_2$, 7%), 287 (M$^+$-Py-3•Me$_2$C=CH$_2$, 11%), 79 (Py$^+$, 100%)

$^1$H-NMR (δ against TMS, C$_6$D$_6$, 300 MHz, 300 K): 8.57 (d, $^3J_{HH}$=4.9 Hz, 2H, o-Py), 6.77 (t, $^3J_{HH}$=7.7 Hz, 1H, p-Py), 6.45 (pseudo-t, $^3J_{HH}$=6.7 Hz, 2H, m-Py), 6.17(broad s, 2H, CH-D$^t$BuAD), 1.55 (s, 9H, $^t$BuN), 1.34 (broad s, 18H, $^t$Bu-D$^t$BuAD)

$^{13}$C{$^1$H}-NMR (C$_6$D$_6$, 75 MHz, 300 K): 150.7, 137.5 and 124.0 (Py), 65.5 (CMe$_3$N), 56.6 (CMe$_3$-D$^t$BuAD), 34.2 (NCMe$_3$), 30.9 (CMe$_3$-D$^t$BuAD)

$^{13}$C{$^1$H}-NMR (d$_8$-toluene, 400 MHz, 230 K): 152.9, 139.9 and 126.8 (Py), 111.8 and 101.4 (CH-D$^t$BuAD), 68.1 (NCMe$_3$), 59.0 and 58.8(CMe$_3$-D$^t$BuAD), 36.7 (NCMe$_3$), 33.5 and 33.0 (CMe$_3$-D$^t$BuAD)

IR (KBr, cm$^{-1}$): 3075(w), 3040(w), 1604(w), 1504(w), 1458(s), 1444(m), 1359(m), 1354(m), 1275(s), 1251(w), 1217(s), 1145(m), 1145(w), 1064(w), 1045(w), 1012(w), 871 (w), 814(w), 771(m), 761(m), 723(w), 698(m), 636(w), 567 (w), 538(w), 507(w).

Example 2

Production of (D$^t$BuAD)($^t$BuN)Ta(NH$^t$Bu) from [($^t$BuN)($^t$BuNH)TaCl$_2$($^t$BuNH$_2$)]$_2$ 1.26 g of D$^t$BuAD (7.5 mmol) were added to the yellow solution of 3.50 g (3.7 mmol) of [($^t$BuN)($^t$BuNH)TaCl$_2$ ($^t$BuNH$_2$)]$_2$ (produced according to Lit. K. C. Javaratne, G. P. A. Yap, B. S. Haggerty, A. L. Rheingold, C. H. Winter, *Inorg. Chem.* 1996, 35, 4910-4920) in 40 ml of THF. The mixture was then stirred for approx. 30 min at 23° C. 0.19 g (7.8 mmol) of magnesium powder were then added and stirred for a further 10 h at 23° C. Following complete dissolution of the Mg the THF was drawn off at 20 mbar and the remaining yellow oil extracted twice with 25 ml of hexane. After evaporating off the hexane, sublimation at 80° C./10$^{-2}$ mbar resulted in the product as a pale yellow solid. Yield: 1.54 g (60% of theoretical), melting point 70° C.

Analysis:

$^1$H-NMR (C$_6$D$_6$, 300 MHz, 300 K): 5.62 (s, 2H, CH-D$^t$-BuAD), 3.41 (s, 1H, NH), 1.56 (s, 9H, N$^t$Bu), 1.32 (s, 18H, $^t$Bu-D$^t$BuAD), 1.27 (s, 9H, NH$^t$Bu)

$^{13}$C{$^1$H}-NMR (C$_6$D$_6$, 75 MHz, 300 K): 102.6 (CH-D$^t$-BuAD), 64.9 (NCMe$_3$), 55.7 (CMe$_3$-D$^t$BuAD), 53.5 (NH-CMe$_3$), 35.3 (NCMe$_3$),35.2(NHCMe$_3$), 32.0 (CMe$_3$-D$^t$-BuAD)

IR (KBr, cm$^{-1}$): 3246(w), 3030(w), 1504(w), 1456(s), 1388(w), 1361(s), 1352(m), 1280(s), 1221(s), 1140(m), 1107 (w), 1072(w), 1037(w), 1024(w), 985(m), 960(w), 920(w), 870(m), 816(w), 781(w), 771(m), 756(w), 590(w), 567(m), 527(m), 445(w).

Example 3

Production of (D$^t$BuAD)($^t$BuN)Ta(NH$^t$Bu) from ($^t$BuN)($^t$BuNH)TaCl$_2$.2Py Instead of [($^t$BuN)($^t$BuNH)TaCl$_2$($^t$BuNH$_2$)]$_2$, ($^t$BuN) ($^t$BuNH)TaCl$_2$.2PY (2.05 g=3.7 mmol, intermediate example B) was used as the starting material with an otherwise identical procedure. Yield 1.22 g=67% of theoretical, melting point 70° C.

Elemental analysis:

Calculated (%) for $C_{18}H_{39}N_4Ta$ (M=492.49 g mol$^{-1}$): C, 43.90; H, 7.98; N, 11.3. Found (%): C, 42.56;.H, 7.89; N, 10.88.

MS-EI: 492 (M$^+$, 33%), 477 (M$^+$-Me, 100%), 436 (M$^+$-Me$_2$C=CH$_2$, 10%), 421 (M$^+$Me-Me$_2$C=CH$_2$, 10%), 380 (M$^+$-2•Me$_2$C=CH$_2$, 1%), 365 (M$^+$-Me-2•Me$_2$C=CH$_2$, 2%), 309 (M$^+$-Me-3•Me$_2$C=CH$_2$, 1%)

Other spectroscopic data ($^1$H-NMR, $^{13}$C{$^1$H}-NMR and IR) as in Example 2.

Example 4

Production of (D$^t$BuAD)($^t$BuN)Ta(NH$^t$Bu) (Direct Synthesis from TaCl$_5$)

145.84 ml of tert-butylamine (1.40 mol) were added dropwise with cooling to a suspension of 50.0 g of TaCl$_5$ (139.58 mmol) in 500 ml of toluene. After stirring for 8 h at 23° C. the yellow solution was filtered and the solvent drawn off at 20 mbar. The oily intermediate was dissolved in 250 ml of THF with no further purification, then 23.49 g (139.6 mmol) of D$^t$BUAD, followed by 3.39 g of Mg powder (139.6 mmol), were added. The reaction mixture was stirred for 12 h at 23° C., then the solvent was drawn off at 20 mbar. The double extraction of the residue with 150 ml of hexane each time produced a yellow, oily raw product which was purified by sublimation at 80° C./10-2 mbar. Yield 35.7 g (52% of theoretical), melting point 70° C.

Spectroscopic data ($^1$H-NMR, $^{13}$C{$^1$H}-NMR and IR) as in Example 2.

Example 5

Production of (D$^t$BuAD)($^t$BuN)Ta(O$^t$Bu) from (D$^t$-BuAD)($^t$BuN)Ta(NH$^t$Bu)

A solution of 0.75 g of tert-butanol (10.15 mmol) in 100 ml of hexane was added dropwise to a solution of 5.00 g (10.15 mmol) of (D$^t$BuAD)($^t$BuN)Ta(NH$^t$Bu) from Example 2 in 100 ml of hexane at −80° C. The reaction mixture was then stirred for 3 h at 23° C. The solvent was drawn off at 20 mbar and the colourless product sublimated at 100° C./10$^{-2}$ mbar. Yield: 4.65 g (93% of theoretical), melting point 79° C.

Elemental analysis:

Calculated (%) for $C_{18}H_{39}N_3OTa$ (M=493.47 g mol$^{-1}$): C, 43.81; H, 7.76; N, 8.52. Found (%): C, 42.89; H, 7.88; N, 8.29.

MS-EI: 493 (M$^+$, 44%), 478 (M$^+$-Me, 21%), 437 (M$^+$-Me$_2$C=CH$_2$, 5%), 422 (M$^+$-Me-Me$_2$C=CH$_2$, 100%), 381 (M$^+$-2•Me$_2$C=CH$_2$, 60%), 366 (M$^+$-Me-2•Me$_2$C=CH$_2$, 5%), 310 (M$^+$-Me 3•Me$_2$C=CH$_2$, 2%)

$^1$H-NMR (δ against TMS, C$_6$D$_6$, 300 MHz, 300 K): 5.82 (s, 2H, CH-D$^t$BuAD), 1.54 (s, 9H, N$^t$Bu), 1.33 (s, 9H, O$^t$Bu), 1.32 (s, 18H, $^t$Bu-D$^t$BuAD)

$^{13}$C{$^1$H}-NMR (C$_6$D$_6$, 75 MHz, 300 K): 104.4 (CH-DAD), 55.9 (CMe$_3$-D$^t$BuAD), 35.3 (s, NCMe$_3$), 33.3 (OCMe$_3$), 32.0 (CMe$_3$-D$^t$BuAD)

IR: (υ, cm$^{-1}$) 3034(w), 1586(w), 1361(s), 1286(s), 1261 (w), 1223(s), 1188(s), 1142(m), 1072(w), 1008(s), 959(w), 920(w), 869(m), 806(m), 789(m), 772(m), 722(w), 563(w), 529(w), 514(w), 471(w).

Example 6

Production of (D$^t$BuAD)($^t$BuN)Ta(O$^t$Bu) from (D$^t$-BuAD)($^t$BuN)TaCl(Py)

42 mg (0.37 mmol) of $^t$BuOK in 10 ml of THF were added to 200 mg (0.37 mmol) of (D$^t$BuAD)($^t$BuN)TaCl(Py) from Example 1 in 10 ml of TBF at −80° C. After stirring for 5 h at 23° C. the solvent was distilled off at 20 mbar. The brown, oily residue was sublimated at 100° C./10$^{-2}$ mbar and produced 95 mg of product (52% of theoretical) with a melting point of 79° C.

Spectroscopic data ($^1$H-NMR, $^{13}$C-NMR, IR) identical to Example 5.

Example 7

Production of (D$^t$BuAD)($^t$BuN)Ta(AcAc) from (D$^t$-BuAD)(N$^t$Bu)Ta(NH$^t$Bu)

0.20 g of acetyl acetone (2.0 mmol), dissolved in 10 ml of hexane, were added to a solution of 1.00 g (2.0 mmol) of (D$^t$BuAD)($^t$BuN)Ta(NH$^t$Bu) from Example 4 in 10 ml of hexane at −80° C. The reaction mixture was then stirred for 5 h at 23° C. After distilling off the solvent at 20 mbar 0.97 g (92% of theoretical) of the analytically pure product were isolated as an orange-coloured powder, melting point 99.1° C.

MS-EI: 519 (M$^+$, 74%), 504 (M$^+$-Me, 43%), 448 (M$^+$-Me$_2$C=CH$_2$, 3%), 57 ($^t$Bu$^+$, 100%)

$^1$H-NMR (δ against TMS, C$_6$D$_6$, 300 MHz, 300 K): 6.04 (s, 2H, CH-D$^t$BuAD), 5.06 (s, 1H CH—AcAc), 1.60 (s, 6H, Me-AcAc), 1.56 (s, 18H, $^t$Bu-D$^t$BuAD), 1.47 (s, 9H, N$^t$Bu)

$^{13}$C{$^1$H}-NMR (C$_6$D$_6$, 75 MHz, 300 K): 191.7 (CO—AcAc), 103.6 (CH—AcAc), 103.4 (CH-D$^t$BuAD), 55.7 (CMe$_3$-D$^t$BuAD), 54.2 (NCMe$_3$), 34.3 (NCMe$_3$), 31.5 (CMe$_3$-D$^t$BuAD), 26.1 (Me-AcAc)

IR(KBr, cm$^{-1}$): 1590(m), 1530(m), 1281(m), 1262(w), 1223(m), 1137(w), 1093(w), 1026(w), 968(w), 933(w), 861 (w), 804(w), 762(w), 722(w), 665(w), 566(w), 534(w), 432 (w).

Example 8

Production of (D$^t$BuAD)($^t$BuN)Ta(AcAc) from (D$^t$-BuAD)Ta(N$^t$Bu)Cl(Py)

640 mg (1.2 mmol) of (D$^t$BuAD)Ta(N$^t$Bu)Cl(Py) from Example 1 were dissolved in 15 ml of THF. To this was added a suspension of 146 mg (1.2 mmol) of sodium acetyl acetonate in 10 ml of THF at −80° C. After heating to 23° C. and stirring for 10 h at this temperature, the solvent was distilled off at 20 mbar. The brown, oily residue was extracted with hexane and crystallised out of hexane, producing 0.28 g (50% of theoretical) of orange-coloured crystals with a melting point of 99° C.

Analysis: Spectroscopic data (MS, $^1$H-NMR, $^{13}$C-NMR and IR) identical to Example 8.

Example 9

Production of (D$^t$BuAD)($^t$BuN)TaBz as Pyridine Complex

A suspension of 210 mg of benzyl magnesium chloride THF complex (0.94 mmol) in 10 ml of diethyl ether was added to 500 mg (0.94 mmol) of [(D$^t$BuAD)($^t$BuN)TaCl(Py)] from Example 1, dissolved in 10 ml of diethyl ether, at −80° C. After 10 min the orange-coloured reaction mixture was heated to 23° C. and stirred at this temperature for 5 h. The yellow precipitate that was formed was then filtered off and washed with 5 ml of diethyl ether. Drying and subsequent recrystallisation from hexane produced 210 mg (38% of theoretical) of pure product as orange-coloured crystals, melting point 117.7° C.

MS-EI: 511 (M$^+$-Py, 3%), 52 (100%)

$^1$H-NMR (δ against TMS, C$_6$D$_6$, 300 MHz, 300 K): 8.21 (d, $^3$J$_{HH}$=3.1 Hz, 2H, o-Py), 6.91 (t, $^3$J$_{HH}$=7.6 Hz, 1H, m-Bz), 6.72-6.62 (m, 4H, o- and p-Bz overlapped with p-Py), 6.30 (pseudo-t, $^3$J$_{HH}$=6.7 Hz, 2H, m-Py), 6.06 (s, 2H, CH—D$^t$-BuAD), 2.10 (broad s, 2H, CH$_2$-Bz), 1.58 (s, 9H, N$^t$Bu), 1.26 (broad s, 18H, $^t$Bu-DAD)

$^{13}$C{$^1$H}-NMR (C$_6$D$_6$, 75 MHz, 300 K): 153.8 (C$_i$-Bz), 150.2 (o-Py), 136.7 (p-Py), 127.2 (m-Bz), 126.5 (o-Bz), 123.8 (m-Py), 119.5 (p-Bz), 104.8 (CH-D$^t$BuAD), 65.5 (NCMe$_3$), 56.3 (CMe$_3$-D$^t$BuAD), 53.6 (CH$_2$-Bz), 34.8 (NCMe$_3$), 31.2 (Ce3-D$^t$BuAD)

IR (KBr, cm$^{-1}$): 3057(w), 1602(w), 1591(w), 1361(w), 1276(m), 1262(w), 1218(m), 1172(w), 1152(w), 1137(w), 1094(w), 1071(w), 1058(w), 1040(w), 1028(w), 1014(m), 986(w), 960(w), 867(w), 805(m), 764(w), 747(w), 723(w), 693(w), 631(w), 592(w), 557(w), 538(w), 503(w).

Example 10

Production of (D$^t$BuAD)($^t$BuN)TaBz from (D$^t$-BuAD)($^t$BuN)Ta(O$^t$Bu)

0.50 g (1.0 mmol) of (D$^t$BuAD)($^t$BuN)Ta(O$^t$Bu) from Example 6 and 0.22 g (1.0 mmol) of benzyl magnesium chloride THF complex (BzMgCl*THF) were mixed at 23° C. This mixture of solids was dissolved in 20 ml of THF and the solution obtained was stirred for 12 h at 23° C. THF was then removed in vacuo (rotary evaporator) and the remaining oil extracted with 10 ml of hexane. Hexane was distilled off and the product distilled (150° C./10$^{-4}$ mbar). Yield: 0.14 g (27%) as a light yellowish liquid.

MS-EI: 511 (M$^+$, 23%), 496 (M$^+$-Me, 32%), 420 (M$^+$-Bz, 5%), 363 ([D$^t$BuAD)TaN]hu +, 13%), 57 ($^t$Bu$^+$, 100%)

$^1$H-NMR (C$_6$D$_6$, 200 MHz, 300 K): 7.22-6.90 (m, 5H, Bz), 5.66 (s, 2H, CH-D$^t$BuAD), 2.01 (s, 2H, CH$_2$-Bz), 1.62 (s, 9H, N$^t$Bu), 1.18 (s, 18H, $^t$Bu-D$^t$BuAD)

$^{13}$C{$^1$H}-NMR (C$_6$D$_6$, 50 MHz, 300 K): 143.2, 128.4, 127.4 and 122.4 (arom. Bz), 103.1 (CH-D$^t$BuAD), 65.4 (NCMe$_3$), 57.6 (CH$_2$-Bz), 57.1 (CMe$_3$-D$^t$BuAD), 35.0 (NCMe$_3$), 31.3 (CMe$_3$-D$^t$BuAD).

IR (KBr, cm$^{-1}$): 3071(w), 3051(w), 3015(m), 2965(s), 2940(s), 2924(s), 2897(s), 2866(m), 1593(s), 1483(s), 1470 (m), 1456(m), 1402(w), 1391(m), 1375(m), 1363(s), 1354(s), 1283(s), 1221(s), 1179(w), 1138(s), 1107(w), 1076(w), 1030 (m), 1018(m), 993(w), 963(m), 872(s), 820(m), 808(w), 787 (w), 777(s), 747(s), 694(s), 625(w), 565(m), 523(s), 451(m).

Example 11

Production of (D$^t$BuAD)($^t$BuN)TaBz from [(D$^t$-BuAD)($^t$BuN)Ta(μ-Cl)]$_2$

Instead of (D$^t$BuAD)($^t$BuN)Ta(O$^t$Bu), 0.46 g of [(D$^t$-BuAD)($^t$BuN)Ta(μ-Cl)]$_2$ from intermediate Example C (1.00 mmol, calculated as monomeric compound) were used as the starting material with otherwise the same procedure as in Example 14. Yield 1.22 g=74% of theoretical.

Analytical data (MS, $^1$H-NMR, $^{13}$C-NMR, IR) identical to Example 10.

Example 12

Production of (D$^t$BuAD)($^t$BuN)TaCp from (D$^t$BuAD)(N$^t$Bu)TaCl(Py)

A solution of 40 mg of cyclopentadienyl lithium (0.56 mmol) in 5 ml of THF was added dropwise to 300 mg (0.56 mmol) of (D$^t$BuAD)(N$^t$Bu)TaCl(Py) from Example 1 in 5 ml of THF at −80° C. At the end of the addition the reaction mixture was heated to 23° C. and stirred for a further 3 h at this temperature. The THF was then distilled off at 20 mbar and the dark, oily residue extracted twice with 15 ml of hexane. Recrystallisation with hexane and subsequent sublimation at 90° C. and 10$^{-2}$ mbar produced 130 mg (48% of theoretical) of analytically pure product with a melting point of 65.3° C.

Elemental analysis:
Calculated (%) for $C_{19}H_{34}N_3Ta$ (M=485.45 g mol$^{-1}$): C, 47.01; H, 7.06; N, 8.66. Found (%): C, 45.03; H, 7.06; N, 7.93.

MS-EI: 485 (M$^+$, 55%), 470 (M$^+$-Me, 100%), 429 (M$^+$-Me$_2$C=CH$_2$, 2%), 414 (M$^+$-Me-Me$_2$C=CH$_2$, 16%), 373 (M$^+$-2•Me$_2$C=CH$_2$, 2%), 358 (M$^+$-Me-2•Me$_2$C=CH$_2$, 8%), 317 (M$^+$-3•Me$_2$C=CH$_2$, 10%), 302(M$^+$-Me-3•Me$_2$C=CH$_2$, 3%)

$^1$H-NMR (δ against TMS, C$_6$D$_6$, 300 MHz, 300 K): 5.67 (s, 2H, CH-D$^t$BuAD), 5.66 (s, 5H, C$_5$H$_5$), 1.30 (s, 9H, N$^t$Bu), 1.25 (s, 18H, $^t$Bu-D$^t$BuAD)

$^{13}$C{$^1$H}-NMR (C$_6$D$_6$, 75 MHz, 300 K): 108.3 (CH-D$^t$BuAD), 100.8 (C$_5$H$_5$), 55.5 (CMe$_3$-D$^t$BuAD), 34.1 (NCMe$_3$), 31.9 (CMe$_3$-D$^t$BuAD)

IR (KBr, cm$^-$): 3028(w), 1506(w), 1358(m), 1274(s), 1221(s), 1156(w), 1095(w), 1061(w), 1013(w), 958(w), 865 (w), 795(s), 766(m), 722(w).

Example 13

Production of (D$^t$BuAD)($^t$BuN)TaCp from CpTa(N$^t$Bu)Cl$_2$

A solution of 940 mg of Li$_2$D$^t$BuAD (5.15 mmol) in 20 ml of THF was added dropwise to 2.00 g (5.15 mmol) of CpTa(N$^t$Bu)Cl$_2$ (produced according to Lit. S. Schmidt, J. Sundermeyer, J. Organomet. Chem. (1994), 472(1-2), 127-38) in 20 ml of THF at −80° C. At the end of the dropwise addition, the batch was heated to 23° C. by removing the cooling and stirred at this temperature for 8 h. The THF was then drawn off at 20 mbar and the product extracted with 30 ml of hexane. Sublimation at 120° C./0.01 mbar produced 500 mg (20.0% of theoretical) of (D$^t$BuAD)($^t$BuN)TaCp as a yellow solid.

Spectroscopic data ($^1$H-, $^{13}$C-NMR and IR spectra) identical to Example 12.

Example 14

Production of (D$^t$BuAD)($^t$BuN)TaInd

A solution of indenyl lithium (114 mg, 0.93 mmol) in 10 ml of THF was added to 500 mg of (D$^t$BuAD)($^t$BuN)TaCl(Py) (0.93 mmol) from Example 1 in 10 ml of THF at −80° C. and the reaction mixture was then stirred for 8 h at 23° C. THF was distilled off at 20 mbar and the complex extracted twice with 15 ml of hexane each time. Removing the hexane by distillation at 20 mbar produced 300 mg (60% of theoretical) of the analytically pure product. Melting point 147.3° C.

Elemental analysis:
Calculated (%) for $C_{23}H_{36}N_3Ta$ (M=535.51 g mol$^{-1}$): C, 51.59; H, 6.78; N, 7.85. Found (%): C, 50.39; H, 6.79; N, 7.56.

MS-EI: 535 (M$^+$, 44%), 520 (M$^+$-Me, 87%), 464 (M$^+$-Me-Me$_2$C=CH$_2$, 7%), 367 (M$^+$-3-Me$_2$C=CH$_2$, 4%), 352 (M$^+$-Me-3•Me$_2$C=CH$_2$, 3%), 57 ($^t$Bu$^+$, 100%)

$^1$H-NMR (δ against TMS, C$_6$D$_6$, 300 MHz, 300 K): 7.17 (d, 2H, J$_{H-H}$=2.9 Hz, Ind), 6.92 (t, 1H, J$_{H-H}$=3.2 Hz, Ind), 6.92 (dd, 2H, J$_{H-H}$=3.2 Hz, J$_{H-H}$=2.9 Hz, Ind), 6.14 (d, 2H, J$_{H-H}$=3.2 Hz, Ind), 5.11 (s, 2H, CH-D$^t$BuAD), 1.28 (s, 27H, N$^t$Bu overlapping with $^t$Bu-D$^t$BuAD)

$^{13}$C{$^1$H}-NMR (C$_6$D$_6$, 75 MHz, 300 K): 123.1, 122.8 and 110.6 (Ind), 107.4 (CH-D$^t$BuAD), 84.8 (Ind), 64.5 (NCMe$_3$), 55.8 (CMe$_3$-D$^t$BuAD), 34 (NCMe$_3$), 31.8 (CMe$_3$-D$^t$BuAD)

IR (KBr, cm$^-$): 3075(w), 3038(w), 1504(w), 1464(s), 1360 (m), 1329(w), 1279(s), 1248(w), 1221(s), 1157(w), 1095(w), 1064(w), 1038(w), 1026(w), 932(w), 868(m), 814(m), 783(s), 771(m), 740(w), 735(m), 600(w), 559(w).

Example 15

Production of (D$^t$BuAD)(DipN)Ta(NHDip)

A solution of 0.72 g of DipNH$_2$ (4.0 mmol) in 10 ml of hexane was added dropwise to a solution of 1.00 g (2.0 mmol) of (D$^t$BuAD)($^t$BuN)Ta(NH$^t$Bu) from Example 2 in 10 ml of hexane at 0°C. The reaction mixture was stirred for 24 h at 23° C. The solution was then concentrated by evaporation to 5 ml and left to stand. After separating off the first crystals the solution was cooled to −30° C., causing the product to crystallise out. Filtration produced 0.64 g (45% of theoretical) of product with a melting point of 149.8° C.

Elemental analysis:
Calculated (%) for $C_{34}H_{55}N_4Ta$ (M=700.79 g mol$^{-1}$): C, 58.27; H, 7.91; N, 7.99. Found (%): C, 57.43; H, 7.93; N, 7.90.

MS-EI: 700 (M$^+$, 100%), 524 (M$^+$-DipNH, 56%)

$^1$H-NMR (δ against TMS, C$_6$D$_{6, 300}$ MHz, 300 K): 7.19-6.92 (m, 6H, Dip), 5.67 (s, 2H, CH-D$^t$BuAD), 4.69 (broad s, 1H, NH), 3.97 and 3.47 (sept, 2H, $^3$J$_{HH}$+6.7 Hz, CH-DipN and CH-DipNH) 1.27 (s, 18H, $^t$Bu-D$^t$BuAD), 1.24 and 1.22 (d, 12H, $^3$J$_{HH}$=6.7 Hz, CH$_3$-DipN overlapping with CH$_3$-DipNH)

$^{13}$C{$^1$H}-NMR (C$_6$D$_6$, 75 MHz, 300 K): 145.8, 142.8, 141.0, 123.7, 122.9, 122.5 and 122.0 (arom. DipNH and DipN), 102.9 (CH-D$^t$BuAD), 57.9 (CMe$_3$-D$^t$BuAD), 31.1 (CMe$_3$-D$^t$BuAD), 29.2 and 27.9 (CH-DipNH and CH-DipN), 24.4 and 23.6 (CH$_3$-DipNH and CH$_3$-DipN)

IR (KBr, cm$^{-1}$): 3270(m), 3048(w), 3032(w), 1620(w), 1588(w), 1431(m), 1364(s), 1323(w), 1296(w), 1251(w), 1221(s), 1159(w), 1142(m), 1115(w), 1099(w), 1074(w), 1057(w), 1045(w), 1024(w), 988(m), 963(w), 934(w), 889 (w), 876(m), 864(w), 818(w), 802(w), 797(w), 777(w), 770 (w), 750(m), 723(w), 698(w), 583(w), 567(w), 521(w), 446 (w).

Example 16

Production of (D$^t$BuAD)($^t$BuN)Ta(BH$_4$)

2.00 g (4.39 mmol, calculated as monomeric compound) of [(D$^t$BuAD) ($^t$BuN)Ta(μ-Cl)]$_2$ from intermediate example C and 0.17 g of NaBH4 (4.39 mmol) were suspended in 50 ml of THF and stirred for 12 h at 23° C. THF was distilled off at 20 mbar and the product extracted with 20 ml of hexane. The solvent was evaporated off from the extract and the remaining red oil sublimated at 60° C./10$^{-4}$ mbar. The sublimation produced 1.64 g (86% of theoretical) of pale yellow, solid product with a melting point of 69.5° C.

Elemental analysis:

Calculated (%) for $C_{14}H_{33}BN_3Ta$ (M=435.20 g mol$^{-1}$): C, 38.64; H, 7.64; N, 9.66. Found (%):

C, 38.86; H, 7.71; N, 9.47.

MS-EI: 435 (M$^+$, 11%), 420 (M$^+$-Me, 7%), 406 (M$^+$-Me-BH$_3$, 13%), 378 (M$^+$-H-Me$_2$C=CH$_2$, 5%), 365 (M$^+$-BH$_3$-Me$_2$C=CH$_2$, 2%), 58 ($^t$BuH$^+$, 100%)

$^1$H-NMR (δ against TMS in $C_6D_6$, 500 MHz, 300 K): 5.91 (s, 2H, CH-D$^t$BuAD), 1.73 (q, 4H, $^1J_{BH}$=85 Hz, BH$_4$), 1.41 (s, 9H, N$^t$Bu), 1.24 (s, 18H, $^t$Bu-D$^t$BuAD)

$^{13}$C{$^1$H}-NMR ($C_6D_6$, 125 MHz, 300 K): 105.8 (CH-DAD), 65.8 (NCMe$_3$), 57.0 (CMe$_3$-D$^t$BuAD), 34.5 (NCMe$_3$), 31.8 (CMe$_3$-D$^t$BuAD)

$^{11}$B—NMR ($C_6D_5CD_3$, 160 MHz, 300 K): +20.2 (pent, $^1J_{BH=85}$ Hz, BH4)

IR (KBr, cm$^{-1}$): 3041(w), 2519(s), 2326(w), 2284(w), 2097(w), 2037(s), 1505(w), 1456(s), 1389(m), 1379(s), 1364(s), 1356(s), 1279(s), 1217(s), 1148(s), 1111(w), 1071 (m), 1038(w), 1028(w), 961(m), 916(w), 874(s), 818(s), 810 (w), 775(s), 723(w), 546(w).

Example 17

Production of (D$^t$BuAD)($^t$BuN)Ta($\eta^3$-all)

1.00 g of [(D$^t$BuAD)($^t$BuN)Ta(π-Cl)]$_2$ (2.19 mmol, calculated as monomeric compound) from intermediate example C and 0.48 g of allyl magnesium bromide THF complex (AllMgBr*THF) (2.19 mmol) were dissolved in 20 ml of THF and stirred for 12 h at 23° C. The solvent was then drawn off at 20 mbar. The remaining yellow solid was extracted twice with 10 ml of hexane each time. After removing the solvent in vacuo (20 mbar) sublimation was performed at 80° C./10$^{-4}$ mbar. Yield: 0.74 g (73% of theoretical) of (D$^t$BuAD) ($^t$BuN)Ta(η$^3$-all) as a yellow solid with a melting point of 61.9° C.

Elemental analysis:

Calculated (%) for $C_{17}H_{34}N_3Ta$ (M=461.43 g mol–1): C, 44.25;H, 7.43;N, 9.11. Found (%): C, 43.81; H, 7.37; N, 9.04.

MS-EI: 461 (M$^+$, 53%), 446 (M$^+$-Me, 25%), 420 (M$^+$-all, 22%), 363 ([(D$^t$BuAD)(TaN)]+, 21%), 57 ($^t$Bu$^+$, 100%)

$^1$H-NMR (δ against TMS in $C_6D_6$, 300 MHz, 300 K): 6.44 (pent, 1H, $^3J_{HH}$=11.4 Hz, η$^3$-all), 5.50 (s, 2H, CH-DAD), 2.31 (broad s, 4H, η$^3$-all), 1.36 (s, 18H, $^{tBu-Dt}$BUAD), 1.26 (s, 9H, N$^t$Bu)

$^{13}$C{$^1$H}-NMR ($C_6D_6$, 75 MHz, 300 K): 133.0 (η$^3$-all), 102.3 (CH-D$^t$BuAD), 68.8 (η$^3$-all), 65.4 (NCMe$_3$) 56.2 (CMe$_3$-D$^t$BuAD) 34.4 (NCMe$_3$), 31.8 (CMe$_3$-D$^t$BuAD)

IR (KBr, cm$^{-1}$): 3065(w), 3027(m), 1628(w), 1501(m), 1456(s), 1389(m), 1360(s), 1281(s), 1248(w), 1221(s), 1150 (m), 1109(w), 1063(w), 1016(w), 1003(m), 961(w), 866(m), 841(s), 808(m), 768(s), 723(w), 694(w), 629(w), 563(w).

Example 18

Production of a Ta-containing CVD Coating According to the Invention

After conventional pretreatment a Si wafer (manufacturer: Wacker or Virginia Semiconductor) was placed in a CVD apparatus (Aix 200 from Aixtron AG). First of all a thermal curing step was performed on the Si wafer in the conventional way for purification purposes at 750° C. in an inert carrier gas stream. Then the wafer was cooled to a substrate temperature of 350° C. A coating comprising the Ta starting substances according to the invention was deposited onto the surface obtained in this way. To this end an inert gas stream of $N_2$ was loaded with the various starting materials. The following were used as starting materials: (DAD)($^t$BuN)Ta(BH$_4$) and 1,1-dimethylhydrazine, the 1,1-dimethylhydrazine being commercially available in the appropriate purity for CVD (for example from Akzo Nobel HPMO).

For the production of the Ta-containing coatings according to the invention the following conditions were chosen, for example, with an overall pressure of the CVD reactor of 100 hPa: 0.0005 hPa (DAD)($^t$BuN)Ta(BH$_4$), 3 hPa 1,1-dimethylhydrazine. The N/Ta ratio was thus chosen as 6000. The loaded $N_2$ carrier gas stream with an overall pressure of 100 hPa was then passed over the surface of the Si wafer heated to 350° C. for a period of 1 h. A coating according to the invention with a thickness of 145 nm was obtained. At the end of the exposure time the CVD plant was adjusted to the deposition conditions for a desired further coating or the coating was cooled under an inert carrier gas stream and removed from the CVD reactor.

Example 19

Production of (D$^t$BuAD)($^t$BuN)NbCl as Pyridine Complex

A solution of 2.1 g (11.7 mmol) of Li$_2$D$^t$BuAD from intermediate example A in 20 ml of THF was added dropwise to a solution of 5.0 g (11.7 mmol) of $^t$BuN=NbCl$_3$.2Py (produced in accordance with Lit. J. Sundermeyer, J. Putterlik, M. Foth, J. S. Field, N. Ramesar, Chem. Ber. 1994, 127, 1201-1212) in 20 ml of THF at –80° C. After stirring for 30 min the dark-brown reaction mixture was. heated and stirred for a further 10 h at 23° C. After removing all volatile components by distillation the residue was extracted twice with 10 ml of diethyl ether each time. The ether phases were combined, the ether distilled off and the yellow residue washed with 20 ml of hexane. Yield 3.8 g (72% of theoretical), melting point 115.4° C.

Elemental analysis:

Calculated (%) for $C_{19}H_{34}N_4ClNb$ (M=446.87 g·mol$^{-1}$): C, 51.07; H, 7.67; N, 12.54. Found (%): C, 49.26; H, 7.64; N, 11.84.

MS-EI: 367 (M$^+$-Py, 30%), 352 (M$^+$-Py-Me, 46%), 296 (M$^+$-Py-Me$_2$C=CH$_2$-Me, 3%), 240 (M$^+$-Py-Me-2•Me$_2$C=CH$_2$, 2%), 199 (M$^+$-Py -3•Me$_2$C=CH$_2$, 13%),57 (100%).

$^1$H-NMR (δ against TMS, $C_6D_6$, 300 MHz, 300 K): 8.53 (pseudo-d, $^3J_{HH}$=3.6 Hz, 2H, o-Py), 6.79 (pseudo-t, $^3J_{HH}$=7.6 Hz, 1H, p-Py), 6.47 (pseudo-t, $^3J_{HH}$=6.3 Hz, 2H, m-Py), 6.17 (broad s, 2H, CH-D$^t$BuAD), 1.52 (s, 9H, $^t$BuN), 1.35 (broad s, 18H, $^t$Bu-D$^t$BuAD)

$^1$H-NMR (δ against TMS, d$_8$-toluene, 100 MHz, 230 K): 8.39 (dd, $^3J_{HH}$=6.4 Hz, $^4J_{HH}$=1.5 Hz, 2H, o-Py), 6.69 (tt, $^3J_{HH}$=7.6 Hz, $^4J_{HH}$=1.5 Hz, 1H, p-pY), 6.38-6.35 (m, 3H, m-Py overlapping with CH-D$^t$BuAD), 5.82 (d, 1H, $^3J_{HH}$=3.5 Hz, CH-D$^t$BuAD), 1.64 (s, 9H, $^t$Bu-D$^t$BuAD), 1.51 (s, 9H, $^t$BuN), 0.96 (broad s, 9H, $^t$Bu-D$^t$BuAD).

$^{13}$C{$^1$H}-NMR ($C_6D_6$, 75 MHz, 300 K): 150.6, 136.9 and 123.7-(Py), 57.3 (CMe$_3$-D$^t$BuAD), 32.9 (NCMe$_3$), 30.7 (CMe$_3$-D$^t$BuAD).

$^{13}$C{$^1$H}-NMR (d$_8$-toluene, 400 MHz, 230 K): 150.1, 137.7 and 123.9 (Py), 110.3 and 101.2 (CH-D$^t$BuAD), 67.0 (NCMe$_3$), 57.0 and 56.6 (CMe$_3$-D$^t$BuAD), 32.7 (NCMe$_3$), 30.5 and 30.2 (CMe$_3$-D$^t$BuAD).

IR (KBr, cm$^{-1}$): 3020(w), 1602(w), 1480(w), 1360(m), 1353(w), 1258(m), 1244(m), 1217(s), 1155(w), 1138(w), 1057(w), 1045(w), 1012(w), 875(m), 814(m), 775(m), 761(m), 723(w), 700(m), 634(w).

Example 20

Production of (D$^r$BUAD)Nb(N$^t$Bu)BH$_4$)

1.6 g (4.35 mmol, calculated as monomeric compound) of [(D$^r$BuAD) ($^t$BuN)Nb(μ-Cl)]$_2$ from intermediate Example E and 0.37 g of NaBH$_4$ (9.78 mmol) were suspended in 50 ml of THF and stirred for 12 h at 23° C. The solvent was distilled off at 20 mbar and the residue sublimated at 60° C./10$^{-4}$ mbar. The sublimation produced 0.95 g (67% of theoretical) of a yellow, solid product with a melting point of 65.4° C.

Elemental analysis:
Calculated (%) for C$_{14}$H$_{33}$BN$_3$Nb (M=347.16 g mol$^{-1}$): C, 48.44; H, 9.58; N, 12.10. Found (%): C, 47.88; H, 9.56; N, 12.11.

MS-EI: 347 (M$^+$, 100%), 332 (M$_+$-Me, 8%), 318 (M$^+$-Me-BH$_3$, 13%), 276 (M$^+$-Me$_2$C=CH$_2$-Me, 42%). $^1$H-NMR (d$_8$-toluene, 500 MHz, 300 K: 5.87 (s, 2H, CH-D$^r$BuAD), 1.31 (s, 9H, N$^t$Bu), 1.19 (s, 18H, $^t$Bu-D$^r$BuAD), 0.04 (q, 4H, $^1J_{BH}$=85 Hz, BH$_4$).
$^{13}$C{$^1$H}-NMR (CD$_6$, 75 MHz, 300 K): 107.8 (CH-D$^r$-BuAD), 33.1 (NCMe$_3$), 31.6 (CMe$_3$-D$^r$BuAD). $^{11}$B—NMR (d$_8$-toluene, 160 MHz, 300 K): -21.3 (quint, $^1J_{BH}$=85 Hz, BH$_4$).

IR (KBr, cm$^{-1}$): 3032(w), 2507(s), 2319(w), 2274(w), 2099(w), 2037(s), 1495(w), 1456(s), 1390(w), 1364(s), 1302(w), 1258(s), 1217(s), 1157(s), 1140(w), 1111(w), 1061(w), 1026(w), 1017(w), 947(w), 876(s), 816(s), 777(s), 723(w), 567(w), 516(w), 513(w), 494(w), 449(w).

Example 21

Production of (D$^r$BuAD)Nb(N$^t$Bu)(NH$^t$Bu)

225 ml of tert-butylamine (2.15 mol) were added dropwise with cooling to a suspension of 50.0 g of NbCl$_5$ (185 mmol) in 300 ml of toluene. After stirring for 8 h at 23° C. the yellow solution was filtered and the solvent drawn off at 20 mbar. The oily intermediate was dissolved in 250 ml of THF with no further purification, and 31.2 g (185 mmol) of D$^r$BuAD, followed by 4.5 g of Mg powder (185 mmol), were then added. The reaction mixture was stirred for 12 h at 23° C., then the solvent was drawn off at 20 mbar. The double extraction of the residue with 250 ml of hexane each time produced a yellow, oily raw product, which was purified by sublimation at 100° C./10$^{-4}$ mbar. Yield: 30.8 g (41% of theoretical), melting point 70.6° C.

Elemental analysis:
Calculated (%) for C$_{18}$H$_{39}$N$_4$Nb (M=404.44 g mol$^{-1}$): C, 53.46; H, 9.72; N, 13.85. Found (%): C, 52.87; H, 9.59; N, 13.56.

MS-EI: 404 (M$^+$, 22%), 389 (M$^+$-Me, 10%), 332 (M$^+$-CH$_3$CNH, 4%), 57 (100%).
$^1$H-NMR (C$_6$D$_6$, 300 MHz, 300 K): 5.86 (s, 2H, CH-D$^r$BuAD), 4.10 (s, 1H, NH), 1.54 (s, 9H, N$^t$Bu), 1.33 (s, 18H, $^t$Bu-D$^r$BuAD), 1.26 (s, 9H, NH$^t$Bu).
$^{13}$C{$^1$H}-NMR (C$_6$D$_6$, 75 MHz, 300 K): 104.2 (CH-D$^r$-BuAD), 64.0 (NCMe$_3$), 55.7 (CMe$_3$-D$^r$BuAD), 53.4 (NH-CMe$_3$), 35.1 (NCMe$_3$), 34.1 (NHCMe$_3$), 31.9 (CMe$_3$-D$^r$-BuAD).

IR (KBr, cm$^{-1}$): 3021(w), 1456(w), 1389(w), 1361(m), 1260(s), 1242(w), 1221(s), 1148(w), 1136(w), 1107(w), 1064(w), 1024(w), 980(w), 950(w), 870(w), 814(w), 771(w), 754(w), 592(w), 572(w), 515(w).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A compound of the formula (I)

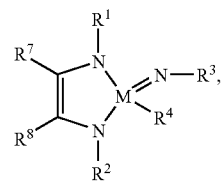

(I)

wherein
M stands for Ta or Nb,
R$^1$ and R$^2$ mutually independently denote optionally substituted C$_1$ to C$_{12}$ alkyl, C$_5$ to C$_{12}$ cycloalkyl or C$_6$ to C$_{10}$ aryl radicals, 1-alkenyl, 2-alkenyl, 3-alkenyl or triorganosilyl radicals —SiR$_3$, or amino radicals NR$_2$ wherein R stands for a C$_1$ to C$_4$ alkyl radical,
R$^3$ denotes an optionally substituted C$_1$ to C$_8$ alkyl, C$_5$ to C$_{10}$ cycloalkyl, C$_6$ to C$_{14}$ aryl radical, or SiR$_3$, or NR$_2$ wherein R has the aforementioned meaning,
R$^4$ denotes (a) halogen selected from the group consisting of Cl, Br, and I,
(b) NH—R$^5$ where R$^5$=optionally substituted C$_1$ to C$_8$ alkyl, C$_5$ to C$_{10}$ cycloalkyl or C$_6$ to C$_{10}$ aryl radical,
(c) O—R$^6$ where R$^6$=optionally substituted C$_1$ to C$_{11}$ alkyl, C$_5$ to C$_{10}$ cycloalkyl or C$_6$ to C$_{10}$ aryl radical,
(d) —SiR$_3$,
(e) BH$_4$,
(f) an optionally substituted allyl radical,
(g) an indenyl radical,
(h) optionally substituted benzyl radical,
(i) an optionally substituted cyclopentadienyl radical,
(j) —NR—NR'R" (hydrazido(-1), wherein R, R' and R" mutually independently have the aforementioned meaning of R,
(k) CH$_2$SiMe$_3$,
(l) pseudohalide, or
(m) silylamide —N(SiMe$_3$)$_2$,
R$^7$ and R$^8$ mutually independently denote H, optionally substituted C$_1$ to C$_{12}$ alkyl, C$_5$ to C$_{12}$ cycloalkyl or C$_6$ to C$_{10}$ aryl radicals.
2. The compound according to claim 1, which corresponds to formula II,

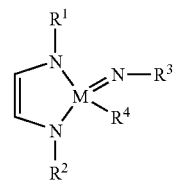

(II)

wherein

M stands for Ta or Nb, $R^1$ and $R^2$ denote identical $C_1$ to $C_5$ alkyl or $C_5$ to $C_6$ cycloalkyl radicals, $R^3$ denotes a $C_1$ to $C_5$ alkyl, $C_5$ to $C_6$ cycloalkyl or optionally substituted phenyl radical, $R^4$ denotes a) halogen selected from the group consisting of Cl, Br, and I, b) a radical NH—$R^5$ where $R^5$=$C_1$ to $C_5$ alkyl, $C_5$ to $C_6$ cycloalkyl or optionally substituted $C_6$ to $C_{10}$ aryl radical, e) $BH_4$, f) an optionally substituted allyl radical, (h) optionally substituted benzyl radical, (i) an optionally substituted cyclopentadienyl radical or an oxyalkyl radical.

3. The compound according to claim 1 corresponding to the formula (III),

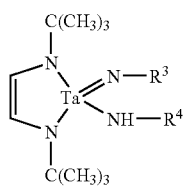
(III)

wherein $R^3$ and $R^4$ mutually independently denote an identical or different radical from the group of $C_1$ to $C_5$ alkyl radicals, or $C_6$ to $C_{10}$ aryl radicals optionally substituted by one to three $C_1$ to $C_5$ alkyl groups.

4. The compound according to claim 2 selected from the group consisting of:

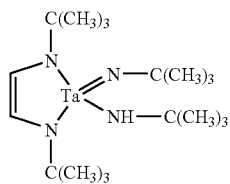
(IV)

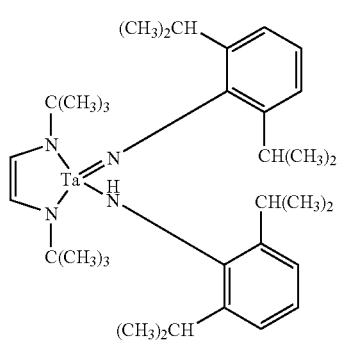
(V)

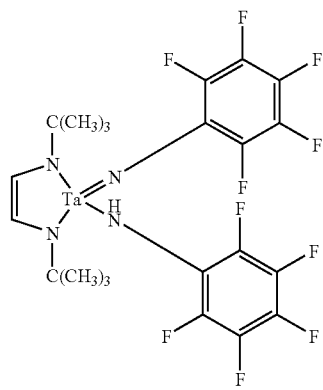
(VI)

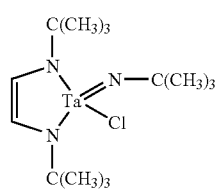
(VII)

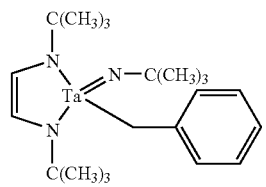
(VIII)

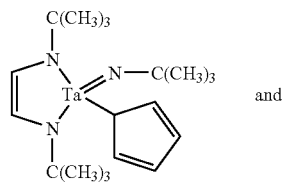
(IX)

and

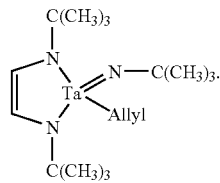
(X)

5. The compound according to claim 2 corresponding to the formula (XI),

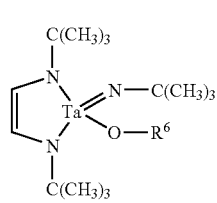
(XI)

wherein $R^6$ denotes an optionally substituted $C_1$ to $C_{12}$ alkyl radical.

6. The compound according to claim 5 corresponding to the structure (XII):

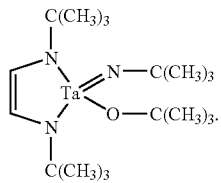

(XII)

7. The compound according to claim 2 corresponding to the structure (XIII),

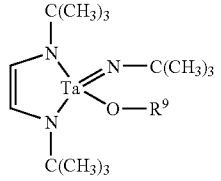

(XIII)

wherein
$R^9$ denotes a radical of an enolate having the formula (XIV),

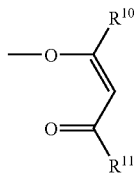

(XIV)

in which
$R^{10}$ denotes a $C_1$ to $C_4$ alkyl radical and $R^{11}$ is the same as $R^{10}$ or mutually independently denotes $OR^{10}$.

8. A tantalum-containing coating which comprise the compound of claim 1.

9. A substrate which comprises the tantalum-containing coating as claimed in claim 8.

10. A niobium-containing coating which comprises the compound of claim 1.

11. A substrate which comprises the niobium-containing coating as claimed in claim 10.

12. A TaN-containing coating which comprises the compound of claim 1.

13. A NbN-containing coating which comprises the compound of claim 1.

* * * * *